United States Patent [19]

Good

[11] Patent Number: 4,495,079

[45] Date of Patent: Jan. 22, 1985

[54] FACIAL SKIN CLEANSER CAPABLE OF SOFTENING AND REMOVING SEBUM PLAQUE

[76] Inventor: Allen H. Good, 149 Kent Place Blvd., Summit, N.J. 07901

[21] Appl. No.: 487,306

[22] Filed: Apr. 21, 1983

[51] Int. Cl.$^3$ ............................ C11D 3/48; C11D 3/46
[52] U.S. Cl. ...................................... 252/106; 252/173; 252/550; 252/DIG. 5; 252/DIG. 14; 514/873
[58] Field of Search ......... 252/106, 550, 173, DIG. 5, 252/DIG. 14; 424/168, 170, 171, 358, 365

[56] References Cited

U.S. PATENT DOCUMENTS

| | | | |
|---|---|---|---|
| 3,829,563 | 8/1974 | Barry et al. | 424/70 |
| 3,860,712 | 1/1975 | Ferrari . | |
| 3,962,150 | 6/1976 | Viola . | |
| 4,140,656 | 2/1979 | Mast . | |
| 4,147,782 | 4/1979 | Klein et al. . | |
| 4,163,800 | 8/1979 | Wickett et al. . | |
| 4,272,544 | 6/1981 | Cella et al. | 424/273 R |
| 4,278,570 | 7/1981 | Flom . | |
| 4,303,543 | 12/1981 | Mansy . | |
| 4,310,433 | 1/1982 | Stiros . | |
| 4,341,799 | 7/1982 | Good | 424/365 |
| 4,368,187 | 1/1983 | Flom . | |

OTHER PUBLICATIONS

"Cosmetics & Toiletries", vol. 95, Apr. 1980, pp. 117, 118, 120 and 121.
"Cosmetics & Toiletries", vol. 92, Mar. 1977, pp. 88-89, William Rosen, and Philip Berke, Germall 115—A Safe and Effective Modern Cosmetic Preservative.

*Primary Examiner*—Prince E. Willis
*Attorney, Agent, or Firm*—Sherman & Shalloway

[57] ABSTRACT

A facial skin cleanser has both moisturizing and cleansing capability provided by a surfactant system which is a mixture of cetyl alcohol, stearyl alcohol, ethoxylated cetyl alcohol, ethoxylated stearyl alcohol and sodium lauryl sulfate and an emollient system composed of a mixture of mineral oil and a mixed acid ester of a higher fatty alcohol esterified with a mixture of caprylic acid and capric acid. These components are dissolved in an aqueous solvent system of water and a minor amount of propylene glycol. The cleanser formulation is thickened with minor amounts of thickening agents exemplified by xanthan gum and carboxypolymethylene. The formulation has a balanced pH and in the range of from about 5.5 to about 7.5. This composition has the capability of softening and removing sebum plaque and exhibits a comedolytic activity while at the same time providing a moisturizing effect to the skin.

10 Claims, No Drawings

FACIAL SKIN CLEANSER CAPABLE OF SOFTENING AND REMOVING SEBUM PLAQUE

This invention relates to a facial skin cleanser useful in the treatment of acne and related skin disorders.

More particularly, this invention relates to a moisturizing facial skin cleanser which is pH balanced, non-allergenic and non-irritating to the skin and which exhibits comedolytic activity.

Keratolytic agents, such as sulfur, resorcinol, salicyclic acid and benzoyl peroxide, have long been known for use in the topical treatment of acne and seborrhea and generally for the topical treatment of skin lesions and other skin ailments associated with over-active sebacous glands and excessively oily skin. Soaps and synthetic detergents have also been routinely used to remove oily secretions and to cleanse the skin of persons suffering from exceptionally oily skin and related disorders. However, these materials cannot be routinely and continuously used as they may cause excessive dryness of the skin or irritation.

Representative of the patent art relating to compositions for the treatment of acne, seborrhea, excessively oily skin and the like are U.S. Pat. Nos. 3,860,712—Ferrari, 4,147,782—Klein and Foxx and 4,163,800—Wickett and Kock. Other patent art relating more generally to cleansing lotions and gels showing the types of cleaning and conditioning agents used in facial skin cleansers and the like include, for example, U.S. Pat. Nos. 4,140,656—Mast, 4,278,570—Flom, 3 962,150—Viola, 4,303,543—Mansy, and 4,310,433—Stiros. One can also refer to various cosmetic formularies such as "Cosmetics and Toiletries", e.g. Cosmetics and Toiletries, Vol. 95, April 1980, pages 117, et seq. for representative dermatological cream and lotion formulations which are available in the art.

Nevertheless, there remains a need for a facial skin cleanser capable of softening and removing sebum plaque which combines moisturizing and cleansing agents but which is non-allergenic and non-irritating to the skin. Still further, there remains a need to provide such a facial skin cleanser composition which can be used with various types of skin, including dry, normal and oily skins and which does not leave a greasy or oily feel on the skin.

Accordingly, it is an object of the present invention to provide a facial skin cleanser capable of softening and removing sebum plaque which is non-irritating to the skin.

It is a further object of the present invention to provide a facial skin cleanser which combines cleansing and moisturizing properties with a nearly neutral pH.

A still further object of the present invention is to provide a facial skin cleanser having comedolytic activity but which is non-irritating to the skin, has a moisturizing effect, a balanced pH, and does not leave a greasy or oily film or feeling on the skin.

Still yet a further object of the present invention is to provide a facial skin cleanser capable of softening and removing sebum plaque while at the same time capable of cleansing a wide variety of substances from the skin including, for example, eye-shadow, mascara, make-up, soil and the like.

SUMMARY OF THE INVENTION

These and other objects of the present invention which will become apparent from the following detailed description are provided by a facial skin cleanser capable of softening or removing sebum plaque which is in the form of a thickened mixture, in an aqueous solvent system, of emollients, and non-irritating nonionic and anionic surface-active agents, the composition having a balanced pH in the range of from about 5.5 to 7.5. The emollient system includes mineral oil and a mixed ester of a higher ($C_{12}$–$C_{18}$) fatty alcohol with caprylic acid and capric acid and the surfactant and cleansing system includes cetyl alcohol, stearyl alcohol, ethoxylated cetyl alcohol and ethoxylated stearyl alcohol as the nonionic components and sodium lauryl sulfate as the anionic surfactant. The preferred aqueous solvent system is a mixture of water and propylene glycol. The preferred thickening system is a mixture of xanthan gum and a carboxy polymethylene component.

The amounts of the emollient and surfactant systems of the facial skin cleanser compositions are of critical importance with regard to providing the combined moisturizing and cleansing properties. The critical amounts of the emollient and surfactant systems of this invention in parts by weight, per 100 parts by weight of the total composition are as follows:

| Ingredients | Numerical Ranges (parts by wt.) |
| --- | --- |
| Mineral Oil | 6 to 20 |
| Mixed ester of $C_{12}$–$C_{18}$ fatty alcohol with Caprylic acid and capric acid | 4 to 19 |
| Mixed cetyl alcohol and stearyl alcohol | 0.02 to 3 |
| Ethoxylated mixture of cetyl alcohol and stearyl alcohol | 0.2 to 3 |
| Sodium lauryl sulfate | 0.02 to 1 |

DETAILED DESCRIPTION OF THE INVENTION

The facial skin cleanser formulation of this invention may be in the form of a lotion, cream or gel as is customarily well known to the cosmetic and dermatological chemist. The form which the cleanser composition will take will depend on such factors as the relative amounts and proportions of the thickening agent system, the amounts and proportions of the surfactants and the amounts and proportion of the solvent system.

Although there are very many available thickening systems for cosmetic formulations, such as the facial skin cleanser of this invention, particularly favorable results in terms of stability and other desirable characteristics have been accomplished using a mixture of xanthan gum and the carboxypolymethylenes (Carbopols) which are crosslinked polymers of acrylic acid as described in U.S. Pat. No. 2,798,053. Briefly, the carboxypolymethylenes are high molecular weight polymers, e.g. usually having a molecular weight greater than 200,000, and preferably greater than 300,000 with the preferred range of molecular weights being between 1,000,000 and 5,000,000. These polymers are available from B. F. Goodrich Company under the trademark "Carbopol" in various grades, including Carbopol 934, Carbopol 940 and Carbopol 941. Carbopol 941 is particularly effective in that it is the clearest and most satisfactory solution.

Xanthan gum is a heteropolysaccharide gum which is a high molecular weight, linear exocellular material prepared by the action of bacteria of the genus Xanthomonas on carbohydrates. Preparation of heteropolysaccharides inclusive of these xanthan gums which can be used in the present invention are described in greater detail, for example, in U.S. Pat. No. 3,020,206. These products are commercially available, for example, from Kelco Company of Clark, N.J., under the tradename Keltrol.

The amount of the xanthan gum thickener preferably ranges from about 0.01 to about 3 parts by weight per 100 parts by weight of the composition and the amount of the carboxypolymethylene thickening agent ranges from about 0.07 to about 0.24 parts by weight per 100 parts by weight of the composition. The more preferred ranges of the xanthan gum and carboxypolymethylene is from about 0.05 to 0.9 parts and from 0.13 to about 0.17 parts, respectively.

The thickening agents and the emollient system and surfactant system are dissolved or dispersed in the aqueous solvent system. In view of the insolubility in water of one or more of the ingredients, such as the higher fatty alcohol, a minor portion of the aqueous solvent system is comprised of a cosmetically acceptable and compatible organic solvent. Propylene glycol has been found to be particularly effective in this regard. Generally, amounts of water in the aqueous system will be in the range of from about 50 to about 75% by weight based on the total composition, preferably from 55 to 65% by weight of the total composition while the amount of propylene glycol will be in the range of from about 3.5 to 6.5 parts by weight, preferably from about 5.0 to 6.0 parts by weight, based on the total composition.

The cleansing function of the composition is provided principally by the surfactant system which is a critical blend of higher fatty alcohols and particularly cetyl alcohol and stearyl alcohol, a portion of which is ethoxylated with from about 10 to about 30, preferably about 22 moles of ethylene oxide. Mixed blends of cetyl alcohol and stearyl alcohol in equal proportions are commercially available under the designation Cetearyl alcohol and such mixed alcohols can preferentially be used in the compositions of this invention. Amounts of Cetearyl alcohol in the range of from about 0.02 to 2.0 parts, preferably from about 0.13 to 0.21 parts, per 100 parts by weight of the composition, are used. Similarly, the ethoxylated blend of cetyl and stearyl alcohols is also commercially available as such and is present in the formulations of the present invention in amounts of from about 0.2 to 3.0 parts, preferably from about 0.7 to 2.0 parts, per 100 parts by weight of the composition. A small amount of sodium lauryl sulfate is present as an anionic surfactant and this ingredient is readily commercially available in various forms and is additionally commercially available as a mixture with Cetearyl alcohol. The amount of sodium lauryl sulfate, on an active basis is from about 0.02 to about 1.0, preferably from about 0.07 to about 0.5 part per 100 parts by weight of the composition.

The emollient system which provides a moisturizing effect for the facial skin cleanser is a critical mixture of mineral oil and a mixed ester of a $C_{12}$–$C_{18}$ fatty alcohol with caprylic acid and capric acid. The fatty alcohol component of this mixed acid preferably has a carbon chain length of from about 12 to 14 carbon atoms. These mixed acids are also commercially available, for example under the tradename Cetiol LC.

The mineral oil can be any cosmetically acceptable grade of mineral oil. The proportions of mineral oil and the mixed capric/caprylic acid ester is important with regard to the presence or absence of a "greasy" or "oily" feel. Generally, the higher the proportion of the mineral oil relative to the mixed acid ester, the greater will be the greasy or oily feel of the composition on the skin. Accordingly, it is preferred in the compositions of this invention that the mineral oil and mixed acid ester be present in a weight ratio of from about 1:0.2 to about 1:1, preferably from about 1:0.7 to about 1:0.9. However, it is understood that the mineral oil can be present in substantially higher proportions without effecting the cleansing quality of the composition, for example, the ability to soften and remove sebum plaque and the comedolytic activity and accordingly, proportions of the mineral oil to the mixed acid ester as high as about 5:1, preferably from about 4:1 and especially preferably from about 2.5:1 are also within the scope of the invention. Within these proportions, the critical amounts of mineral oil is from about 6 to 20 parts by weight, preferably from about 10 to 16 parts by weight, per 100 parts by weight of the composition and the critical amounts of the caprylic acid-capric acid mixed ester of the higher fatty alcohol is from about 4 to 19 parts, and preferably from about 6 to 13 parts, per 100 parts by weight of the composition.

In addition to the critical components which include the surfactant system, emollient system, aqueous solvent system, and appropriate thickeners, other conventional additives in facial cleanser compositions and similar cosmetic formulations which are well known to the cosmetic chemist and dermatological chemist can also be included in the compositions of this invention. In particular, it is highly preferred to include a cosmetic preserving agent such as methylhydroxybenzoate and propyhydroxybenzoate, also known as methyl paraben and propyl paraben, respectively. It is also known in the art that the bactericidal activity of these preserving agents can be synergistically enhanced by blending the parabens with imidazolidinyl urea, which is commercially available under the trade designation Germall 115 from Sutton Laboratories, Inc., Roselle, N.J. Particularly effective systems include from about 0.10 to about 0.25 part methyl paraben, from 0.05 to about 0.10 part propyl paraben and from about 0.20 to about 0.35 part Germall 115.

It is also possible to include small amounts of other adjuvants such as fragrances, coloring agents, foam boosters and the like.

In view of the neutral or slightly acidic pH of the skin, the compositions of this invention are formulated to have a pH in the range of from about 5.5 to about 7.5, preferably from about 6.0 to about 7.0 by the addition of a suitable alkali. Potassium hydroxide is especially preferred for this purpose.

The broad and preferred ranges of the facial skin cleansers are shown in the following Table 1:

TABLE 1

| Ingredient | Preferred Range (wt %) | Broad Range (wt %) |
|---|---|---|
| Aqueous Solvent System | | |
| Water (DI) | 55–65 | 50–75 |
| Propylene glycol | 5.0–6.0 | 3.5–6.5 |
| Thickeners | | |
| Xanthan Gum | .05–.9 | .01–3.0 |
| Carbomer 941 (Carbopol 941) (2%) | 6.5–8.5 | 3.5–12 |
| Emollients | | |
| Mineral Oil | 10–16 | 6–20 |

TABLE 1-continued

| Ingredient | Preferred Range (wt %) | Broad Range (wt %) |
|---|---|---|
| Caprylic-Capric Acid Ester of Fatty Alcohol | 6–13 | 4–19 |
| Surface Active Agents | | |
| Cetearyl Alcohol (Cetyl & Stearyl Alcohol) | .06–.16 | .1–2.0 |
| Cetearyl Alcohol plus Sodium Lauryl Sulfate | .15–1.0 | .05–2.0 |
| Ethoxylated Cetyl/Stearyl Alcohol | .7–2.0 | .2–3.0 |
| pH Modifier | | |
| KOH (10%) sufficient amount to bring to | pH 6.0–7.0 | pH 5.5–7.5 |
| Adjuvants | | |
| Antibacterial agent | | |

EXAMPLE 1

The following composition is prepared:

| | Amount (g) | wt % |
|---|---|---|
| Water (DI) | 280.0 | 62.14 |
| Propylene Glycol | 25.0 | 5.5 |
| Methyl Paraben | 0.7 | 0.16 |
| Propyl Paraben | 0.35 | 0.08 |
| Xanthan Gum | 0.5 | .11 |
| Carbomer 941 (2%) | 35.0 | 7.75 |
| Mineral Oil | 50.0 | 11.06 |
| Caprylic-Capric Acid Ester of Fatty Alcohol | 45.0 | 9.96 |
| Cetyl Alcohol & Stearyl Alcohol (Cetearyl Alcohol) (Equal parts) | .6 | .13 |
| Cetearyl Alcohol plus Sodium Lauryl Sulfate | 3.0 | .66 |
| Ethoxylated Cetyl Stearyl Alcohol | 5.0 | 1.1 |
| KOH 10% | 4.7 | 1.04 |
| Germall 115 (Imidazolidinyl Urea) | 1.4 | 0.31 |
| | 451.25 | 100.0 |

EXAMPLE 2

The composition of Example 1 was tested in the rabbit ear for comedolytic potential, by means of a modification of the methods of Mills and Kligman: Mills, O. and Kligman, A., Assay of Comedolytic Agents in the Rabbit Ear. In: *Animal Models in Dermatology* (Chapt. 18); Maibach, H., Ed., N.Y. Churchill Livingtone (1975), 175–183, and Kligman, A. and Mills, O., Acne Cosmetics, Arch. Derm., (1972) 106: 843–850.

Procedure: Comedo formation was induced by topical administration of 5% coal tar (U.S.P. Tar; Koppers Co., Inc., Pittsburgh, Pa.) in Polylan ® (Amerchol ®; CPC International Inc., Edison, N.J.) to the inner surface of both ears of eight mature New Zealand albino rabbits (both sexes) once daily, five consecutive days/week for two weeks. The test animals were housed in individual stainless steel cages and maintained on Ralston Purina Rabbit Chow Checkers and water ad libitum. The selection of rabbits for use in this test was made on a random basis.

During the following two-week period, the pinna of one ear of each of the rabbits was treated by gentle inunction with 0.5 ml of the test material once daily, five consecutive days/week. The contralateral ear of each rabbit served as an untreated control.

Following two weeks of treatment with the test preparation, the animals were sacrificed. Samples of each ear were excised, using an 8 mm biopsy punch. The tissues were quickly frozen with $CO_2$, sectioned, mounted, stained (H & E), examined microscopically, and graded according to the scale shown in Table 2.

Results: A score was determined for each ear, based on the overall degree of follicular reaction and keratin impaction observed. These scores, as well as mean values, are presented in Table 3.

The treated and control ears of two rabbits (#3 and #6) showed only a minimal degree of distention of the pilosebaceous canal and concomitant keratin retention (scores $\leq 1.0$). On this basis, it was determined that the comedonal development in the control ear was not sufficient to permit an adequate evaluation of the possible comedolytic effects of the test compound in the treated ear. Therefore, while the observed scores for the ears of these two animals are presented in Table 3, these data were not used in the determination of mean values.

Pilosebaceous structures in tissue samples of five of the remaining six treated ears exhibited less overall follicular distention and keratin retention than those of their respective controls.

TABLE 2

| SCALE FOR GRADING COMEDOGENIC CONDITION | |
|---|---|
| 0 | no comedones observed; sebaceous glands appear healthy. |
| 1 | slight distention of pilosebaceous canal, with keratin present in small amounts; sebaceous glands appear healthy. |
| 2 | moderate distention of the pilosebaceous canal, with keratin impactions present in moderate amounts; sebaceous glands appear compressed. |
| 3 | marked distention of the pilosebaceous canal with severe keratin impactions; sebaceous glands extremely compressed or not visible. |

TABLE 3

| | COMEDOGENICITY SCORES | |
|---|---|---|
| RABBIT NO. | TREATED EAR | CONTROL EAR |
| 1 | 2.0 | 3.0 |
| 2 | 0.5 | 2.0 |
| 3* | (1.0) | (1.0) |
| 4 | 3.0 | 1.5 |
| 5 | 1.0 | 3.0 |
| 6* | (0.5) | (1.0) |
| 7 | 1.0 | 3.0 |
| 8 | 1.0 | 3.0 |
| Mean (n = 6) | 1.4 | 2.6 |

*The scores of rabbits Nos. 3 and 6 were excluded from analysis, due to apparently insufficient comedonal development.

From this data, it can be seen that the facial skin cleanser of Example 1 exhibited about a 46% comedolytic activity.

What is claimed is:

1. A facial skin cleanser capable of softening and removing sebum plaque which comprises a thickened mixture of from 6 to 20 parts mineral oil, 4 to 19 parts of a mixed ester of a $C_{12}$–$C_{18}$ fatty alcohol with caprylic acid and capric acid, 0.02 to 3 parts of a mixture of cetyl alcohol and stearyl alcohol, 0.2 to 3 parts of a mixture of cetyl alcohol and stearyl alcohol ethoxylated with from 10 to 30 moles of ethylene oxide, 0.02 to 1 part of sodium lauryl sulfate, per 100 parts by weight of the composition, and sufficient alkali to raise the pH of the composition to from 5.5 to 7.5, the balance comprising an aqueous solvent system.

2. The facial cleanser of claim 1 which comprises 10 to 16 parts mineral oil, 6 to 13 parts of said mixed ester, 0.13 to 0.21 parts of the mixture of cetyl alcohol and stearyl alcohol, 0.7 to 2.0 parts of the ethoxylated mixture, 0.07 to 0.5 part of sodium lauryl sulfate, and an amount of alkali sufficient to raise the pH to 6.0 to 7.0.

3. The facial cleanser of claim 1 which comprises about 0.01 to 3 parts of xanthan gum and about 0.07 to 0.24 part of carboxypolymethylene, per 100 parts by weight of the composition.

4. The facial cleanser of claim 1 wherein the aqueous solvent system comprises water and from about 3.5 to 6.5 parts propylene glycol per 100 parts by weight of the composition.

5. The facial cleanser of claim 2 which comprises about 0.05 to 0.9 part of xanthan gum and about 0.13 to 0.17 part carboxypolymethylene, per 100 parts by weight of the composition.

6. The facial cleanser of claim 2 wherein the aqueous solvent system comprises water and from about 5 to 6 parts propylene glycol per 100 parts by weight of the composition.

7. The facial cleanser of claim 1 which consists essentially of, in parts by weight:

| | |
|---|---|
| water | 280 |
| propylene glycol | 25 |
| xanthan gum | 0.5 |
| carboxypolymethylene (2%) | 35 |
| mineral oil | 50 |
| caprylic-capric acid ester of fatty alcohol | 45 |
| mixed cetyl alcohol and stearyl alcohol | 2 |
| sodium lauryl sulfate | 1.5 |
| ethoxylated cetyl/stearyl alcohol | 5 |
| KOH (10%) | 4.7 |
| preservatives | 2-2.5. |

8. The facial cleanser of claim 7 wherein the preservative comprises, in parts by weight:

| | |
|---|---|
| methyl paraben | 0.7 |
| propyl paraben | 0.35 |
| imidazolidinyl urea | 1.4. |

9. A non-oily, non-greasy facial skin cleanser which is capable of softening and removing sebum plaque, is non-irritating to the skin and which combines cleansing and moisturizing properties with a nearly neutral pH, said cleanser comprising a thickened mixture, in an aqueous solvent system, of emollients and non-irritating non-ionic and anionic surface-active agents, wherein said emollients consist essentially of, per 100 parts by weight of the cleanser, 6 to 20 parts mineral oil and 4 to 19 parts of a mixed ester of a $C_{12}$ to $C_{18}$ fatty alcohol with caprylic acid and capric acid, and wherein said surface-active agents consist essentially of, per 100 parts by weight of the cleanser, 0.02 to 3 parts of a mixture of cetyl alcohol and stearyl alcohol, 0.2 to 3 parts of a mixture of cetyl alcohol and stearyl alcohol ethoxylated with from 10 to 30 moles of ethylene oxide, and 0.02 to 1 part of sodium lauryl sulfate, and wherein said aqueous solvent system comprises, per 100 parts by weight of the cleanser, about 50 to 75 parts water and about 3.5 to 6.5 parts propylene glycol, said cleanser further comprising sufficient alkali to raise the pH of the composition to from 5.5 to 7.5.

10. The cleanser of claim 9 wherein the weight ratio of the mineral oil to the mixed ester is from about 1:0.2 to about 1:1.

* * * * *